United States Patent
Langer et al.

(10) Patent No.: US 7,629,490 B2
(45) Date of Patent: Dec. 8, 2009

(54) PROCESS FOR HYDROLYSING CYCLOPROPANECARBOXYLIC ESTERS TO THE FREE ACID

(75) Inventors: Reinhard Langer, Tönisvorst (DE); Herbert Emde, Köln (DE); Paul Wagner, Düsseldorf (DE)

(73) Assignee: LANXESS Deutschland GmbH, Leverkusen (DE)

(*) Notice: Subject to any disclaimer, the term of this patent is extended or adjusted under 35 U.S.C. 154(b) by 0 days.

(21) Appl. No.: 11/388,875

(22) Filed: Mar. 24, 2006

(65) Prior Publication Data

US 2006/0224014 A1 Oct. 5, 2006

(30) Foreign Application Priority Data

Mar. 30, 2005 (DE) .............. 10 2005 014 310

(51) Int. Cl.
*C07C 61/04* (2006.01)
(52) U.S. Cl. .................................. 562/506
(58) Field of Classification Search .......... 560/124
See application file for complete search history.

(56) References Cited

U.S. PATENT DOCUMENTS 5,371,270 A * 12/1994 Kaufhold et al. ............ 560/124
6,166,247 A    12/2000 Kaufhold
6,462,231 B1 * 10/2002 Yanagawa et al. ........... 562/512

OTHER PUBLICATIONS

Joseph B. Lambert, James J. Napoli, Katharine Kappauf Johnson, Kalulu N. Taba, and Beverly Sue Packard J. Org. Chem. 1985, 50, 1291-1295.*
Bruce, Stanley; Kent, Ronald; *Organic Preparations and Procedures International*, "Improved Two-Step Synthesis of Ethyl Cyclopropanecarboxylate and Cyclopropanecarboxylic Acid", 1974, 6(4), pp. 193-196.
Lambert, Joseph B.; Napoli, James J.; Kappauf Johnson, Katharine; Taba, Kalulu N.; Packard, Beverly Sue; *Journal of Organic Chemistry*, "Scope, Limitations, and Mechanism of the Homoconjugate Electrophilic Addition of Hydrogen Halides," 1985, 50(8), pp. 1291-1295.
Friedhelm Korte: "Methodicum Chimicum," Methodicum Chimicum, 1975, XP002075408, pp. 563-564.

* cited by examiner

*Primary Examiner*—Karl J Puttlitz
(74) *Attorney, Agent, or Firm*—Michael A. Miller

(57) ABSTRACT

The present invention relates to an improved process for preparing cyclopropanecarboxylic acid and alcohols.

19 Claims, 2 Drawing Sheets

PROCESS FOR HYDROLYSING CYCLOPROPANECARBOXYLIC ESTERS TO THE FREE ACID

Figure 1:
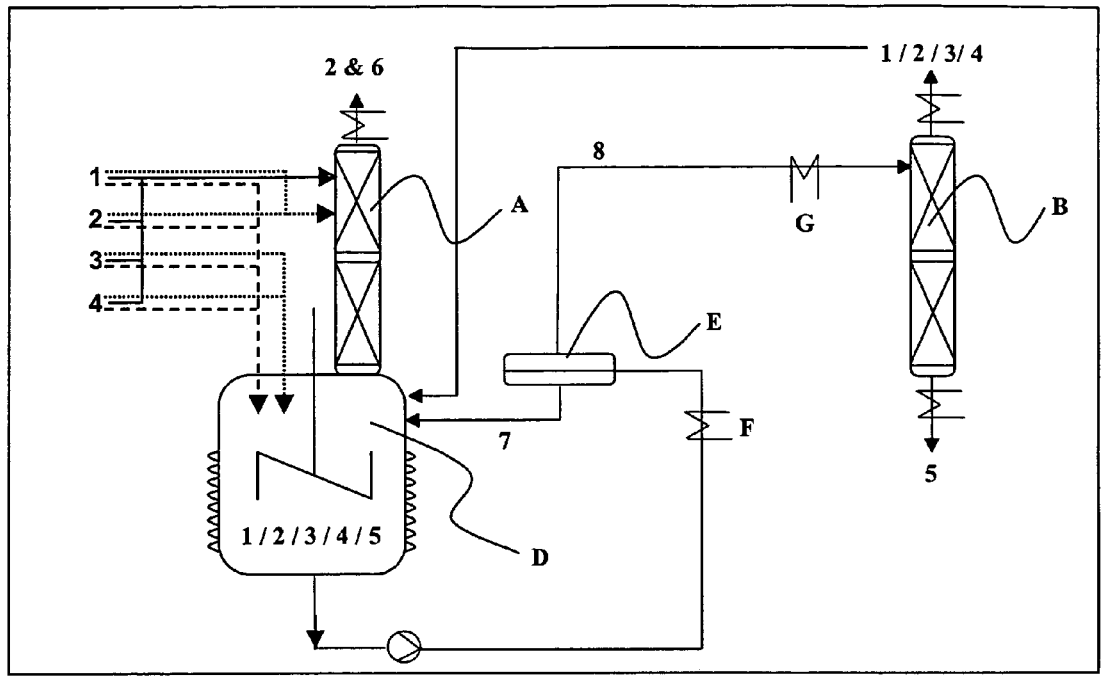

The invention relates to a process for preparing cyclopropanecarboxylic acid and alcohols.

The preparation of cyclopropanecarboxylic acid by acid-catalysed hydrolysis of the methyl or ethyl esters takes place according to the following reaction:

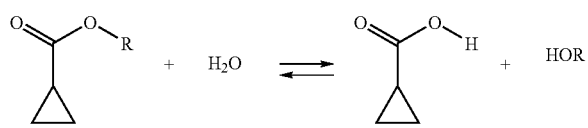

Cyclopropanecarboxylic acid is an important intermediate for the preparation of chemicals, pharmaceutical products and crop protection agents.

Cyclopropanecarboxylic esters are prepared by known methods; for example, the methyl ester is obtained by cyclising methyl 4-chlorobutyrate by means of sodium methoxide, as described, for example, in EP 0 577 949 A1.

The cyclopropanecarboxylic esters can be hydrolysed by means of aqueous alkali metal hydroxide, as described, for example, by Stanley Bruce and Ronald Kent in Organic Preparations and Procedures International (1974), 6(4), pages 193-196.

A disadvantage of this procedure is the inevitable formation of aqueous salt solution from which the product has to be isolated, which can be achieved only by extraction with a solvent; this is complicated due to the high saturation concentration of cyclopropanecarboxylic acid; for example, even a saturated sodium sulphate solution still has a concentration of 3%.

The acid-catalysed hydrolysis of cyclopropanecarboxylic esters suffers from a loss of catalyst and selectivity, since, as described by Lambert, Napoli, Johnson and Taba in Journal of Organic Chemistry (1985), 50(8), 1291-1295, acids such as hydrochloric acid (3) add on to cyclopropanecarboxylic acid and its derivatives to form, for example, 4chlorobutyric acid derivatives.

In EP 0 879 813 A1, Kaufhold overcomes yield losses and formation of salts by transesterifying methyl or ethyl cyclopropanecarboxylates with other clarboxylic acids, preferably formic acid, in the presence of toluenesulphonic acids as catalysts and then, for example, removing methyl formate from the mixture by distillation. In the comparative example, catalysed by sulphuric acid, slight yield losses occur here too. Disadvantages of this process are the need for an acid and the inevitable formation of the ester of this acid.

A simple industrial process in which methyl or ethyl cyclopropanecarboxylate (1) is hydrolysed by means of water (4) and cyclopropanecarboxylic acid and the largely pure alcohol are formed as sole products is unknown and desirable.

It was therefore an object of the present invention to provide a process for preparing cyclopropanecarboxylic acid and alcohols, which saves energy and is more environmentally friendly compared to the prior art and can be carried out continuously and in which cyclopropanecarboxylic acid and alcohol having a high purity can be prepared as sole products in a high yield.

This object is achieved by a process for preparing cyclopropanecarboxylic acid (5), characterized in that methyl or ethyl cyclopropanecarboxylate (1), if appropriate in admixture with one or more alcohols (2), and also with water (4) and, if appropriate, hydrochloric acid (3), is hydrolysed, in which a) methyl or ethyl cyclopropanecarboxylate (1), if appropriate in admixture with one or more alcohols (2), and also with water (4) and, if appropriate, hydrochloric acid (3), are fed, either separately or together, into an apparatus comprising a vessel (D) which may be equipped with an automatic stirrer and is connected to a 1st column (A) provided with a condenser, with the alcohol or alcohols (2) being taken off via the top of the column (A) and either:
  1) methyl or ethyl cyclopropanecarboxylate (1), if appropriate in admixture with one or more alcohols (2), and also with water (4) and, if appropriate, hydrochloric acid (3), being introduced either separately or together into a 1st column (A) provided with a condenser, or
  2) methyl or ethyl cyclopropanecarboxylate (1), if appropriate in admixture with one or more alcohols (2), and also with water (4) and, if appropriate, hydrochloric acid (3), being fed either separately or together into the vessel (D), or
  3) methyl or ethyl cyclopropanecarboxylate (1), if appropriate in admixture with one or more alcohols (2), being introduced into the 1st column (A) provided with a condenser while water (4) and, if appropriate, hydrochloric acid (3) are fed either separately or together into the vessel (D), b) the reaction mixture which goes either directly or in cases a)1) and a)3) either in its entirety or partly via the 1st column (A) into the vessel (D) is subsequently fed to a 2nd column (B) provided with a condenser, with the cyclopropanecarboxylic acid (5) being taken off in the bottoms from the column (B) while the remaining reaction mixture is recirculated to the vessel (D) and, if no hydrochloric acid (3) is used, at least one acidic solid (9) being placed initially in the vessel (D).

The variant a)1) is denoted in the figures by a line ⟶.
The variant a)2) is denoted in the figures by a line ⟶.
The variant a)3) is denoted in the figures by a line ⟶.

If hydrochloric acid (3) is used, the reaction mixture present in the vessel (D) is, if appropriate after cooling (F), subjected to a phase separation (E) to form an organic phase and an aqueous phase (7) in step b) before being fed to the 2nd column (B), with the aqueous phase (7) being introduced into the vessel (D) and the organic phase (8) being introduced into the 2nd column (B) provided with a condenser.

The residue from the 2nd column (B) is preferably either wholly or partly condensed or recirculated in gaseous form to the vessel (D). The vessel (D) is preferably heated.

The reflux ratio (R/R) in the 1st column (A) is preferably from 10/1 to 1/5, particularly preferably from 5/1 to 1/1.

The reflux ratio (R/R) in the 2nd column (B) is preferably from 2/1 to 1/100, particularly preferably from 1/1 to 1/50 and very particularly preferably from 1/2 to 1/30.

To discharge the organic phase, the mixture is preferably cooled (F) to temperatures in the range from 20 to 90° C., preferably from 40 to 70° C., very particularly from 50 to 60° C., prior to the phase separation (E).

The mixtures of methyl or ethyl cyclopropanecarboxylate (1) and alcohols (2) are preferably metered into the 1st column (A), in particular at or in the vicinity of the point where the ratio of methyl or ethyl cyclopropanecarboxylate (1) to the alcohols (2) in the 1st column (A) corresponds to that of the mixture of the starting material.

If the methyl or ethyl cyclopropanecarboxylate (1) is metered in with alcohols (2), the point of introduction is preferably in the lower part of the superposed 1 st column (A).

The 1st column (A) preferably operates at temperatures of from 40 to 130° C., in particular from 60 to 110° C., and under pressures of from 0.1 to 2.0 bar, in particular from 0.5 to 1.2 bar.

The 1st column (A) preferably has from 2 to 300, in particular from 5 to 50, plates.

The 2nd column (B) preferably operates at temperatures of from 40 to 200° C., in particular from 80 to 180° C., and under pressures of from 0.01 to 2.0 bar, in particular from 0.1 to 1.2 bar.

The 2nd column (B) preferably has from 1 to 100, in particular from 3 to 30, plates.

Replacement of the 1st Column (A) and 2nd Column (B) by a 3rd Column (C)

The 1st column (A) and 2nd column (B) are preferably replaced by a 3rd column (C) which is connected to the vessel (D).

The 3rd column (C) is preferably connected on the liquid side and if appropriate on the gas side to the vessel (D). The 3rd column (C) preferably operates at temperatures of from 40 to 200° C., in particular from 60 to 180° C., and under pressures of from 0.01 to 2.0 bar, in particular from 0.1 to 1.2 bar.

The 3rd column (C) has from 5 to 300, in particular from 30 to 60, plates. The reflux ratio (R/R) in the 3rd column (C) is preferably from 10/1 to 1/1, particularly preferably from 5/1 to 2/1.

The 3rd column (C) preferably has a connected reaction vessel as vessel (D). The contents of the reaction vessel (preferably only the organic phase (8)) are preferably fed to the 2nd to 30th plate, particularly preferably to the 3rd to 15th plate, very particularly preferably to the 6th to 10th plate. The liquid flowing downwards in the 3rd column (C) is preferably taken off in its entirety or partly at a point which is from 1 to 10 plates, particularly preferably from 1 to 5 plates, very particularly preferably from 1 to 2 plates, above the point at which the reaction mixture is pumped into the column and is introduced into the reaction vessel.

Cyclopropanecarboxylic ester (1), if appropriate in admixture with the corresponding alcohol (2), hydrochloric acid (3) and water (4) are metered into the reaction vessel, viz. the vessel (D). If the cyclopropanecarboxylic ester (1) is metered in in admixture with alcohol (2), it is preferably introduced into the part of the 3rd column (C) which is located above the offtake point for the reaction vessel, viz. the vessel (D).

Heat is preferably introduced into the reaction vessel as vessel (D) so that vapour (H) is formed and is introduced together with the discharged organic phase into the 3rd column (C).

General Information

The mixture from vessel (D) can preferably be heated and partly vaporized (G) by means of an additional heat exchanger before being fed into the 2nd column (B) or into the 3rd column (C).

The vessel (D) preferably keeps the starting materials at temperatures of from 92 to 110° C., in particular from 96 to 100° C.

The hydrochloric acid concentration (3) in the aqueous phase, after the sample has been cooled to room temperature, is preferably from 4 to 20%, particularly preferably from 7 to 14%, very particularly preferably from 9 to 12%. The hydrochloric acid concentration (3) can, as described in the prior art, be measured by means of sensors and the introduction of hydrochloric acid (3) can be controlled. The appearance and disappearance of a second phase in the vessel (D) (cloud point) is preferably utilized for control. When the turbidity disappears, the amount metered in is increased until the turbidity reoccurs, and the amount metered in is then reduced until it disappears again.

It is likewise possible for the hydrochloric acid (3) to be metered in at a constant rate; the hydrochloric acid concentration (3) is then established via the methyl chloride formation which increases with concentration.

The metered addition of water is controlled via the ratio of the phases after cooling.

If the hydrochloric acid (3) is omitted, which has advantages in terms of the corrosion properties of the mixture, preference is given to using acidic solids (9), particularly preferably sulphonic acid ion-exchange resins such as Lewatit or Nafions. These acidic solids (9) are either introduced into the vessel (D) and retained there by means of screen devices or as pack material (for example Multipack® from Montz) or the vessel (D) is a stationary bed through which the mixture is pumped.

In this process, the water content should not be so high that a second phase occurs, and a phase separation (E) is therefore not necessary. The metered addition of water is therefore regulated, for example, according to the boiling point of the mixture.

The process is preferably carried out continuously, pseudo-continuously or batchwise.

The purity of the cyclopropanecarboxylic acid (5) is preferably >96%, in particular >98%, based on starting materials.

The purity of the alcohol (2) is preferably >98.5%, in particular >99.5%, based on starting materials.

The alcohol (2) is preferably methanol and/or ethanol.

The apparatus is illustrated below with the aid of drawings which show a plurality of embodiments. Here, further inventive features and advantages of the invention can be derived from the drawings and the description.

In the drawings:

FIG. 1: Apparatus for preparing cyclopropanecarboxylic acid (5) and alcohols (2) using hydrochloric acid (3). Here, a vessel (D), a 1st column (A), a 2nd column (B), a phase separation (E), the cooling (F) and a partial vaporization (G) are connected to one another.

Figure 2:
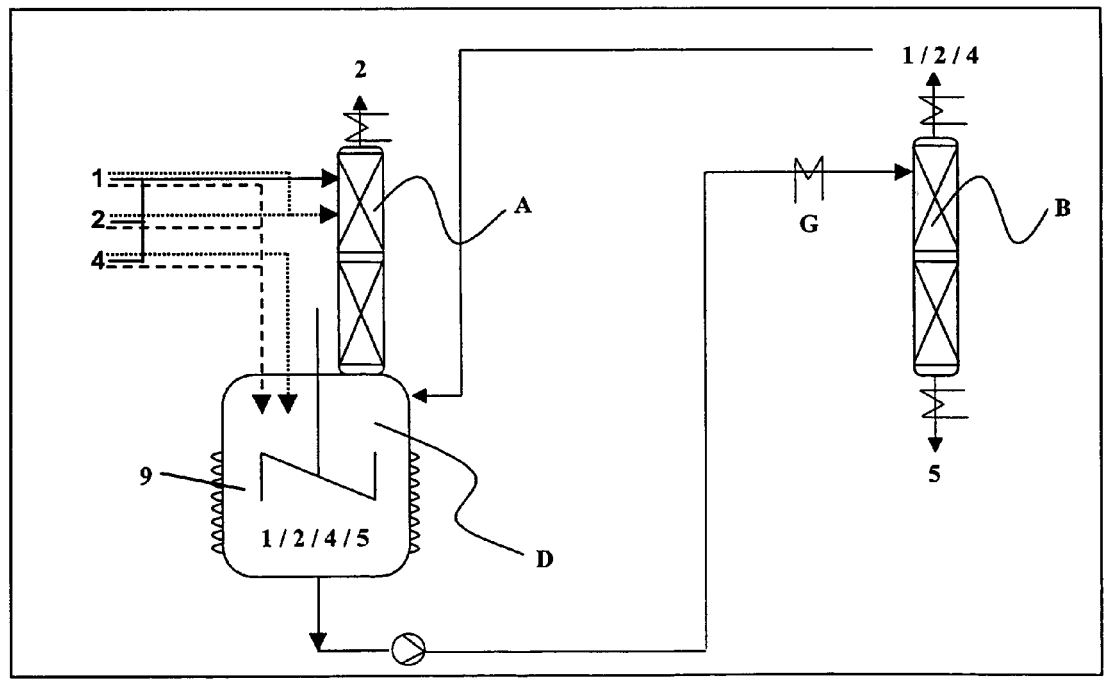

FIG. 2: Apparatus for preparing cyclopropanecarboxylic acid (5) and alcohols (2) using an acidic solid (9) (Lewatit). Here, a vessel (D), a 1st column (A), a 2nd column (B) and a partial vaporization (G) are connected to one another.

Figure 3:
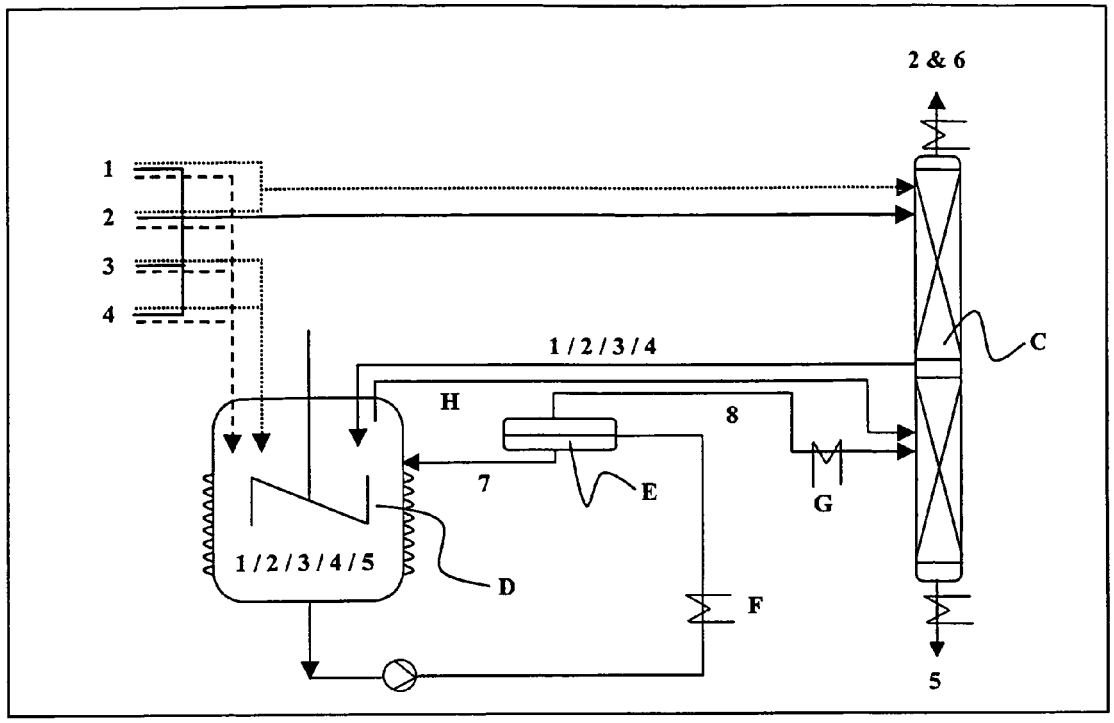

FIG. 3: Apparatus for preparing cyclopropanecarboxylic acid (5) and alcohols (2) using hydrochloric acid (3). Here, a vessel (D), a 3rd column (C), a phase separation (E), the cooling (F) and a partial vaporization (G) are connected to one another.

Figure 4:
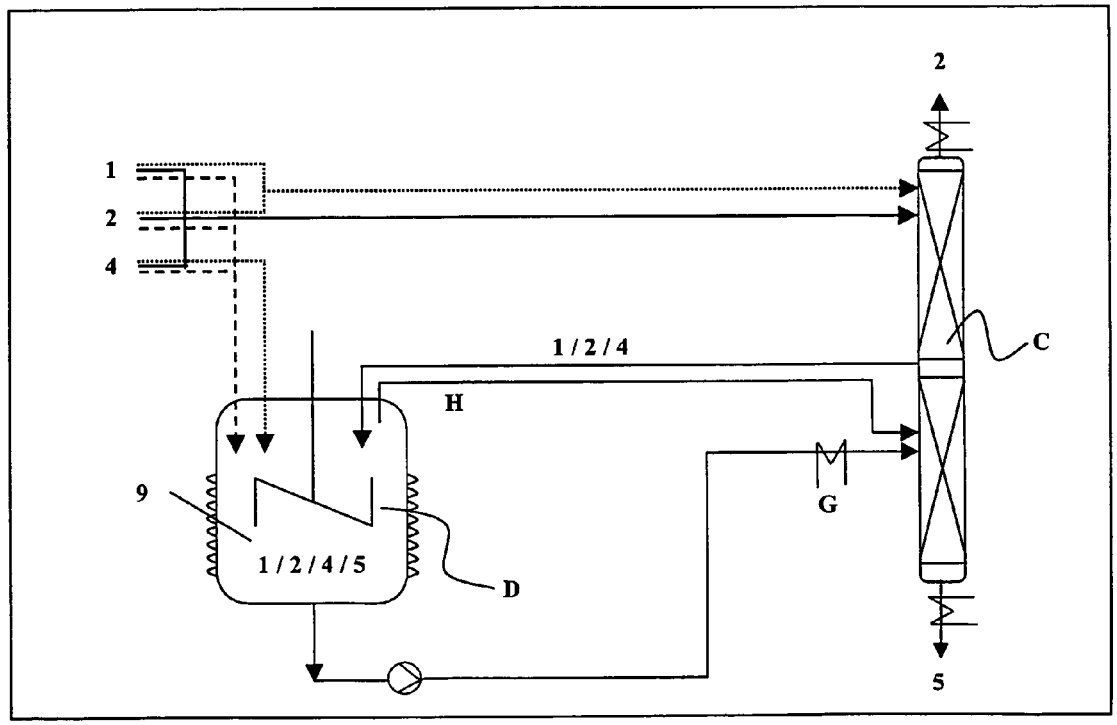

FIG. 4: Apparatus for preparing cyclopropanecarboxylic acid (5) and alcohols (2) using an acidic solid (9) (Lewatit). Here, a vessel (D), a 3rd column (C) and a partial vaporization (G) are connected to one another.

The inventive scope of the present invention is defined not only by the subject matter of the individual claims but also by combinations of the individual claims with one another. The same applies to all parameters disclosed in the description and any combinations thereof.

The invention is illustrated by the following examples without being restricted thereby.

Legend for the Drawings

1. Methyl or ethyl cyclopropanecarboxylate
2. Alcohol
3. Hydrochloric acid

4. Water
5. Cyclopropanecarboxylic acid
6. Methyl chloride
7. Aqueous phase
8. Organic phase
9. Acidic solid
A. 1st column
B. 2nd column
C. 3rd column
D. Vessel
E. Phase separation
F. Cooling
G. Partial vaporization
H. Vapour

EXAMPLES

Measurement Methods

The composition of the mixtures was determined by gas-chromatographic analysis corresponding to the prior art. An HP 6890 with a standard glass capillary column was used as chromatograph. Detection was carried out by means of a flame ionization detector (FID). The detection limit was ±0.1 STANDARD-% (i.e. % by weight but without undetectable components).

The concentration of the hydrochloric acid was determined by means of titration, in the case of traces by means of X-ray fluorescence. The detection limit was ±10 ppm.

The water content was determined by the Karl-Fischer method. The detection limit was ±2% relative (i.e. 2% in the case of pure water and 2 ppm at a water content of 100 ppm).

Example 1 (Hydrochloric Acid (3) Method)

The apparatus was constructed as in FIG. 1 but without a partial vaporization (G) upstream of the stripping section. It comprised an oil-heated 10 l flange pot with stirrer as vessel (D), a superposed column having about 25 plates and a condenser and runback divider as 1st column (A) and a superposed column having about 15 plates and a condenser and runback divider as 2nd column (B). About 550 g/h of methyl cyclopropanecarboxylate (1) and 111 g/h of a 10% strength hydrochloric acid (3) were fed into this flange pot as vessel (D).

About 71 of mixture comprising methanol as alcohol (2), methyl cyclopropanecarboxylate (1), cyclopropanecarboxylic acid (5), hydrochloric acid (3) and water (4) boil in the flange pot as vessel (D) at a boiling point of 94-95° C. At the top of the 1st column (A), methanol which had a purity of >99% and was contaminated with 0.17% of methyl chloride (6) and 0.73% of methyl cyclopropanecarboxylate (1) was taken off at a temperature of 64° C. and an R/R=2. Free hydrochloric acid (3) was present in the distillate at a concentration below the detection limit of 10 ppm. Apart from 180 g/h of methanol, 15 g/h of methyl chloride (6) were liberated, but the major part of the latter was condensed only in a downstream cold trap. The runback divider was controlled by means of a temperature measurement in the middle of the 1st column (A) which set the runback divider to total reflux when 76° C. was exceeded.

The mixture from the vessel (D) was subjected to a phase separation (E). About 1800 g/h of organic phase (8) were cooled to 60° C. and separated off (E) and fed into the upper part of a 15 plate column as 2nd column (B) which was located on an oil-heated 10 l flange pot with overflow in order to collect the methyl cyclopropanecarboxylate (1) as product. The flange pot was charged with about 6 l of a liquid which boiled at 182° C. The 2nd column (B) was superposed by a condenser with reflux divider which was operated with total offtake. The overhead product obtained at 80° C. consisted of two phases and was made up mostly of methyl cyclopropanecarboxylate (1) and water (4) and contained about 10% of methanol and 3.6% of cyclopropanecarboxylic acid (5). About 480 g/h of cyclopropanecarboxylic acid (5) which had no other constituents apart from 2.1% of cyclopropanecarboxylic anhydride left the flange pot.

The aqueous phase (7) of the reactor had a content of (3) of about 11% according to titration. When a 17% strength hydrochloric acid (3) was pumped in, the content of hydrochloric acid (3) increased to 12%. A 37% strength hydrochloric acid (3) led to a content of 14.5% of hydrochloric acid (3). At this content, 0.08% of butyrolactone could be detected in the cyclopropanecarboxylic acid (5). When a 50% strength hydrochloric acid (3) obtained by mixing of water (4) and hydrogen chloride gas (3) was pumped in, the hydrochloric acid (3) content of the aqueous phase rose to 15% and 0.14% of butyrolactone were present in the cyclopropanecarboxylic acid (5). When the process was carried out by alternate introduction of 15% strength hydrochloric acid (3) and 7% strength hydrochloric acid (3) or of 20% strength hydrochloric acid (3) and water (4) at 99.5° C. at the cloud point, the aqueous phase (7) contained about 10% of hydrochloric acid (3) at room temperature.

Example 2 (Acidic Solid (9)—Lewatit Method)

The apparatus was constructed as in FIG. 2 but without a partial vaporization (G) upstream of the stripping section. The mixture in vessel (D) was pumped out of the reactor via a screen in order to leave the Lewatit in the reactor. The 1st and 2nd columns (A and B) and the flange pots were the same as in Example 1. 500 g of a commercial moist sulphonic acid Lewatit (K2431) as acidic solid (9) were present in the reactor. 280 g/h of methyl cyclopropanecarboxylate (1) and 50 g of water (4) were pumped into the reactor. A boiling point of 99° C. was maintained by means of the introduction of water. When the temperature increased, the amount of water introduced was also increased; when the temperature dropped, the amount of water introduced was also decreased. About 95 g/h of methanol containing about 0.2% of methyl cyclopropanecarboxylate (1) was obtained at the top of the 1st column (A) at 65° C. About 700 g/h of reaction mixture were fed into the stripping section. About 240 g/h of cyclopropanecarboxylic acid (5) which, according to analysis by gas chromatography, contained 3.5% of cyclopropanecarboxylic anhydride left the flange pot of the stripping section. The Lewatit as acidic solid (9) displayed no drop in activity even after 1000 h.

The invention claimed is:

1. Process for preparing cyclopropanecarboxylic acid comprising hydrolyzing methyl or ethyl cyclopropanecarboxylate in admixture with one or more alcohols, optionally, hydrochloric acid, wherein the concentration of the hydrochloric acid is from 4 to 20% in the aqueous phase, wherein
 a) the methyl or ethyl cyclopropanecarboxylate one or more alcohols, water, and, optionally, hydrochloric acid are fed, either separately or together, into an apparatus comprising a vessel connected to a 1st column provided with a condenser, where the alcohol or alcohols taken off via the top of the column wherein, step a) is carried out by one of the following variants:
  1) the methyl or ethyl cyclopropanecarboxylate, one or more alcohols, water, and, optionally, hydrochloric acid are introduced either separately or together into the 1st column, or 2) the methyl or ethyl cyclopropanecarboxylate, one or more alcohols, water, and, optionally, hydrochloric acid are fed either separately or together into the vessel, or 3) the methyl or ethyl cyclopropanecarboxylate and, one or more alcohols are introduced into the 1st column and where the water and, optionally, hydrochloric acid are fed either separately or together into the vessel, b) the reaction mixture which goes either directly or in cases a) 1) and a) 3) either in its entirety or partly via the 1st column into the vessel is subsequently fed to a 2nd column provided with a condenser, wherein the cyclopropanecarboxylic acid is taken off from the bottom of the 2nd column while the remaining reaction mixture is recirculated to the vessel and, if no hydrochloric acid is used, at least one acidic solid being placed initially in the vessel.

2. Process according to claim 1, characterized in that if hydrochloric acid is used, the reaction mixture present in the vessel is subjected to a phase separation to form an organic phase and an aqueous phase in step b) before being fed to the 2nd column, wherein the aqueous phase is introduced into the vessel and the organic phase is introduced into the 2nd column.

3. Process according to claim 1, characterized in that mixtures of methyl or ethyl cyclopropanecarboxylate and alcohols are metered into the 1st column where the ratio of methyl or ethyl cyclopropanecarboxylate to the alcohols in the 1st column corresponds to that of the mixture of the starting material.

4. Process according to claim 1, characterized in that the 1st column operates at temperatures of from 40 to 130° C., and under pressures of from 0.1 to 2.0 bar.

5. Process according to claim 1, characterized in that the 1st column has from 2 to 300 plates.

6. Process according to claim 1, characterized in that the 2nd column operates at temperatures of from 40 to 200° C. and under pressures of from 0.01 to 2.0 bar.

7. Process according to claim 1, characterized in that the 2nd column has from 1 to 100.

8. Process according to claim 1, characterized in that the 1st column and the 2nd column are replaced by a 3rd column connected to the vessel.

9. Process according to claim 8, characterized in that the 3rd column is connected on the liquid side of the vessel.

10. Process according to claim 8, characterized in that the 3rd column operates at temperatures of from 40 to 200° C. and under pressures of from 0.01 to 2.0 bar.

11. Process according to claim 8, characterized in that the 3rd column has from 5 to 300 plates.

12. Process according to claim 1, characterized in that the vessel keeps the starting materials at temperatures of from 92 to 110° C.

13. Process according to claim 1, characterized in that a sulphonic acid ion-exchange resin is used as acidic solid.

14. Process according to claim 1, characterized in that the purity of the cyclopropanecarboxylic acid is >96% based on the starting materials.

15. Process according to claim 1, characterized in that the purity of the alcohol is >98.5% based on the starting materials.

16. Process according to claim 1, characterized in that the alcohol is methanol.

17. Process for preparing cyclopropanecarboxylic acid comprising hydrolyzing methyl or ethyl cyclopropanecarboxylate in admixture with one or more alcohols and water, wherein b) the methyl or ethyl cyclopropanecarboxylate, one or more alcohols and water are fed, either separately or together, into an apparatus comprising a vessel connected to a 1st column provided with a condenser, where the alcohol or alcohols are taken off via the top of the column wherein, step a) is carried out by one of the following variants:

4) the methyl or ethyl cyclopropanecarboxylate, one or more alcohols and water are introduced either separately or together into the 1st column, or 5) the methyl or ethyl cyclopropanecarboxylate, one or more alcohols and water are fed either separately or together into the vessel, or 6) the methyl or ethyl cyclopropanecarboxylate and one or more alcohols are introduced into the 1st column and where the water is fed separately together into the vessel, b) the reaction mixture which goes either directly or in cases a)1) and a)3) either in its entirety or partly via the 1st column into the vessel is subsequently fed to a 2nd column provided with a condenser, wherein the cyclopropanecarboxylic acid is taken off from the bottom of the 2nd column while the remaining reaction mixture is recirculated to the vessel and at least one acidic solid being placed initially in the vessel.

18. The process according to claim 17, wherein the acid solid comprises a sulphonic acid ion-exchange resin.

19. Process for preparing cyclopropanecarboxylic acid comprising hydrolyzing methyl or ethyl cyclopropanecarboxylate in admixture with one or more alcohols and water, wherein c) the methyl or ethyl cyclopropanecarboxylate, one or more alcohols and water are fed, either separately or together, into an apparatus comprising a vessel connected to a 1st column provided with a condenser, where the alcohol or alcohols are taken off via the top of the column wherein, step a) is carried out by one of the following variants:

7) the methyl or ethyl cyclopropanecarboxylate, one or more alcohols and water are introduced either separately or together into the 1st column, or 8) the methyl or ethyl cyclopropanecarboxylate, one or more alcohols and water are fed either separately or together into the vessel, or 9) the methyl or ethyl cyclopropanecarboxylate and one or more alcohols are introduced into the 1st column and where the water is fed separately together into the vessel, b) the reaction mixture which goes either directly or in cases a)1) and a)3) either in its entirety or partly via the 1st column into the vessel is subsequently fed to a 2nd column provided with a condenser, wherein the cyclopropanecarboxylic acid is taken off from the bottom of the column while the remaining reaction mixture is recirculated to the vessel and wherein a sulphonic acid ion-exchange resin is placed initially in the vessel.

* * * * *